(12) United States Patent
Baumann et al.

(10) Patent No.: US 9,474,439 B2
(45) Date of Patent: Oct. 25, 2016

(54) OBSERVATION INSTRUMENT COMPRISING A HIGH-RESOLUTION IMAGE RECORDER

(71) Applicant: Karl Storz GmbH & Co. KG, Tuttlingen (DE)

(72) Inventors: Harald Baumann, Tuttlingen (DE); Joachim Reinacher, Tuttlingen (DE)

(73) Assignee: Karl Storz GmbH & Co. KG, Tuttlingen (DE)

( * ) Notice: Subject to any disclaimer, the term of this patent is extended or adjusted under 35 U.S.C. 154(b) by 246 days.

(21) Appl. No.: 14/079,037

(22) Filed: Nov. 13, 2013

(65) Prior Publication Data
US 2014/0135577 A1 May 15, 2014

(30) Foreign Application Priority Data

Nov. 13, 2012 (DE) .......................... 10 2012 110 905

(51) Int. Cl.
| | |
|---|---|
| A61B 1/00 | (2006.01) |
| A61B 1/06 | (2006.01) |
| A61B 1/055 | (2006.01) |
| G02B 23/24 | (2006.01) |
| G02B 5/04 | (2006.01) |

(52) U.S. Cl.
CPC ............ *A61B 1/055* (2013.01); *A61B 1/00096* (2013.01); *A61B 1/00179* (2013.01); *G02B 23/243* (2013.01); *G02B 5/04* (2013.01)

(58) Field of Classification Search
CPC .......... A61B 1/00096; A61B 1/00179; A61B 1/055; G02B 23/243; G02B 5/04
USPC ......... 600/104–107, 109, 170–171, 173–174
See application file for complete search history.

(56) References Cited

U.S. PATENT DOCUMENTS

| | | | | |
|---|---|---|---|---|
| 4,140,364 A | * | 2/1979 | Yamashita ......... | A61B 1/00165 359/367 |
| 4,573,450 A | * | 3/1986 | Arakawa ............ | A61B 1/00177 348/65 |
| 4,746,203 A | * | 5/1988 | Nishioka .................. | A61B 1/05 348/E5.027 |
| 5,237,446 A | * | 8/1993 | Takahashi .......... | G02B 27/1006 348/337 |
| 5,416,638 A | * | 5/1995 | Broome ................. | A61B 1/055 348/E7.087 |
| 5,454,366 A | | 10/1995 | Ito et al. | |

(Continued)

FOREIGN PATENT DOCUMENTS

| | | |
|---|---|---|
| DE | 19750640 A1 | 5/1998 |
| DE | 102005008153 A1 | 11/2005 |

(Continued)

*Primary Examiner* — John P Leubecker
*Assistant Examiner* — Arnaldo Torres Diaz
(74) *Attorney, Agent, or Firm* — Whitmyer IP Group LLC

(57) ABSTRACT

An instrument includes a hollow body with an internal diameter and an optoelectronic image recording system, which is arranged in an end region of the body and has a lens system on an image entrance side. The lens system has a cylindrical section and an image sensor. An external diameter of the cylindrical section is less than the internal diameter of the body, such that an interspace remains between an inner side of the body and an outer side of the lens system, providing access in the body for components. With a viewing direction of 0° to 90° from the optical axis of the lens system, a deflection prism is arranged on the image entrance side at the lens system, and has a section extending laterally beyond the external diameter of the cylindrical section. An image entrance plane of the image sensor runs approximately parallel to the optical axis.

20 Claims, 5 Drawing Sheets

(56) References Cited

U.S. PATENT DOCUMENTS

| | | | | |
|---|---|---|---|---|
| 5,720,706 | A * | 2/1998 | Takahashi | A61B 1/00179 348/45 |
| 5,751,341 | A * | 5/1998 | Chaleki | A61B 1/00045 348/45 |
| 5,892,630 | A * | 4/1999 | Broome | G02B 23/2423 359/656 |
| 5,894,369 | A | 4/1999 | Akiba et al. | |
| 5,902,232 | A * | 5/1999 | Igarashi | A61B 1/002 359/434 |
| 5,980,453 | A * | 11/1999 | Forkey | A61B 1/00193 600/162 |
| 6,641,530 | B2 * | 11/2003 | Mitsumori | A61B 1/00096 600/130 |
| 7,280,283 | B1 | 10/2007 | Kasai | |
| 7,542,211 | B2 * | 6/2009 | Togino | G02B 17/0848 348/335 |
| 8,913,112 | B2 * | 12/2014 | Nagamizu | A61B 1/00163 348/65 |
| 8,992,423 | B2 * | 3/2015 | Hale | A61B 5/04525 382/276 |
| 2002/0027723 | A1 * | 3/2002 | Lei | G02B 23/243 359/691 |
| 2002/0082476 | A1 * | 6/2002 | Takahashi | G02B 23/2415 600/173 |
| 2002/0091305 | A1 * | 7/2002 | Lederer | G02B 23/2423 600/171 |
| 2003/0107823 | A1 | 6/2003 | Sekiyama et al. | |
| 2004/0190154 | A1 * | 9/2004 | Wakai | G02B 13/0045 359/676 |
| 2005/0020876 | A1 * | 1/2005 | Shioda | A61B 1/00039 600/101 |
| 2006/0173242 | A1 | 8/2006 | Navok et al. | |
| 2007/0024739 | A1 | 2/2007 | Konno | |
| 2008/0165424 | A1 * | 7/2008 | Togino | G02B 17/0848 359/637 |
| 2009/0270683 | A1 * | 10/2009 | Farr | G02B 25/001 600/166 |
| 2010/0231702 | A1 | 9/2010 | Tsujimura et al. | |
| 2011/0184239 | A1 * | 7/2011 | Wright | A61B 1/00016 600/118 |
| 2011/0199471 | A1 * | 8/2011 | Tomioka | G02B 23/2423 348/65 |
| 2011/0292195 | A1 | 12/2011 | Dahmen | |
| 2012/0184819 | A1 * | 7/2012 | Farr | G02B 25/001 600/166 |
| 2013/0044361 | A1 * | 2/2013 | Katakura | A61B 1/00183 359/226.1 |
| 2013/0184525 | A1 * | 7/2013 | Kojima | A61B 1/051 600/109 |
| 2013/0211199 | A1 | 8/2013 | Navok et al. | |
| 2013/0314521 | A1 * | 11/2013 | Satake | A61B 1/00096 348/76 |

FOREIGN PATENT DOCUMENTS

| | | |
|---|---|---|
| DE | 102009020262 A1 | 11/2010 |
| EP | 2392248 A2 | 12/2011 |
| JP | S61254917 A | 11/1986 |
| WO | 2006066022 A2 | 6/2006 |
| WO | 2009041723 A1 | 4/2009 |

* cited by examiner

OBSERVATION INSTRUMENT COMPRISING A HIGH-RESOLUTION IMAGE RECORDER

BACKGROUND OF THE INVENTION

The invention relates to an observation instrument comprising a hollow body having a specific internal diameter, wherein an optoelectronic image recording system is arranged in an end region of the hollow body and has on the image entrance side an optical lens system having a cylindrical section and subsequently an image sensor, which converts the image coming from the optical lens system into electrical image signals, wherein the optical axis of the lens system extends in the direction of the longitudinal axis of the hollow body, wherein the external diameter of the cylindrical section of the lens system is less than the internal diameter of the hollow body, to be precise such that between an inner side of the hollow body and the outer side of the optical lens system a sufficient interspace remains, through which further components can be led in the hollow body, wherein with a viewing direction of greater than 0° to less than 90° from the optical axis of the image system a distal deflection prism is arranged on the image entrance side at the lens system.

Such observation instruments comprising a hollow body in the form of a shank are used in particular as endoscopes or as exoscopes. DE 10 2010 007 394 A1 discloses a medical observation instrument having an optoelectronic image recording system arranged in its shank in the distal end region.

In numerous observation instruments, the viewing direction runs straight ahead, that is to say that it runs in the longitudinal axis of the shank. In some fields of use, particularly in the medical field, however, it is desirable for such observation instruments to have a viewing direction which deviates from the rectilinear viewing direction, the so-called 0° viewing direction, wherein the viewing direction deviates from the rectilinear viewing direction by between 0° and up to 90°.

As a result, cavities, such as the interior of a bladder, for example, can be examined spaciously, particularly if the rectilinearly and longitudinally extending shank has to be introduced through a channel of long extent, for example a urethra, into said cavity to be observed.

The optical axis of the actual lens system that guides the entering image to the optical sensor extends in the direction of the longitudinal axis of the shank. As a result, it is possible to produce the lens systems by means of customary lenses having a circular cross section.

In order that the light or image arriving from the inclined viewing direction can then be fed to this lens system extending in the optical axis, a distal deflection prism is arranged on the image entrance side at the lens system. Said deflection prism has the task of feeding the light or image rays arriving at the respective viewing angle of between 0° and 90° to the optical lens system as far as possible in the direction of the optical axis.

In the case of these observation instruments, the image is projected by the optical lens system onto an image sensor that converts the optical image information into electrical image signals. Said electrical image signals are then fed via corresponding lines to an image conversion system or to a monitor.

The technology of image sensors has undergone considerable development in recent years, particularly as far as the resolution is concerned. In this regard, high-resolution image sensors having pixel sizes of less than 3 μm are already commercially available at the present time.

The hollow shanks of observation instruments have a diameter which is substantially determined by the size of the opening through which the shank of the observation instrument can be led.

Particularly in the medical field, said openings are predefined by specific organs, for example by the diameter of a urethra or the anatomy of the person in whom observation is to take place.

In this regard, by way of example, shanks that can be used for children have significantly smaller diameters than those for adults. In the ENT field and also in brain surgery, often only openings or channels having very small diameters are available for introducing such hollow shanks of observation instruments.

In numerous cases, the observation instrument is not just purely an observation instrument, rather medical interventions are intended also to be able to be performed by means of the shank. Therefore, the optoelectronic image recording system cannot occupy the entire inner lumen of the hollow body, but rather only parts thereof, such that alongside the optoelectronic image recording system a sufficiently large interspace also remains for leading through further components.

Since, by way of example, instruments are led through said interspace, which instruments carry away contaminated tissue from inside the body after the intervention through the shank, it is necessary to ensure that hermetic sealing between the optoelectronic image recording system and said interspace is effected, in order that no contaminations or contaminants can penetrate into this system. Furthermore, this system has to be hermetically separated from the interspace additionally because said interspace has to be rinsed, cleaned and disinfected after an intervention. The chemically aggressive media used in this case might damage the optoelectronic system.

Therefore, the so-called multi-tube technique is employed in this technology. That means that the optoelectronic image recording system is integrated into an inner shank, which is introduced into the actual hollow body, which is then designated as the outer shank. In this case, customary arrangements include those in which the inner shank is either arranged coaxially in the outer shank, such that a ring-shaped interspace remains around its outer side, through which interspace further components or instruments or else other shanks can then be led. Alternatively, the inner shank is arranged along a surface line on the inner side of the outer shank, such that a crescent-like interspace remains. Accordingly, the external diameter of the cylindrical section of the lens system usually corresponds to the internal diameter of an inner shank inserted into the actual hollow body.

In the observation systems having viewing directions that deviate from the rectilinear 0° viewing direction, the distal deflection prism is required. Since the latter is likewise arranged in the optoelectronic image recording system hermetically sealed from the interspace, its radial extent is likewise restricted to the diameter of the cylindrical section since it is accommodated in said inner shank or a corresponding sleeve surrounding said section of the optical system.

It has now been established that as a result of the further development of the high-resolution image sensors by means of such an optoelectronic image recording system, the image information conducted to the image sensor is less than the latter could actually handle. The high resolution is determined by the so-called numerical aperture, that is to say the angle formed by an image beam which impinges on a pixel point of the image sensor. The higher the numerical aperture, that is to say the greater said angle, the sharper and more highly resolved the pixel.

It has now been established in practical use that with the predefined dimensions, that is the diameter of the optical lens system, the amount of image information that can be conducted to a high-resolution image sensor is not as much as the latter can acquire.

One solution to the problem would be to increase the diameter of the optical lens system with the image recording area and resolution of an image sensor remaining the same. This is impractical, however, since otherwise the interspace between the optoelectronic image recording system and the inner side of the hollow body would become small, and so instruments could no longer be led through or not enough optical fibres for the illumination could be led to distal.

As already mentioned, the size or the diameter of the outer shank is determined by the opening into which such a shank of an observation instrument can be inserted. In the field of technical endoscopy, by way of example that would include existing holes, for example for examining the interior of a combustion chamber or the like, which cannot be enlarged for any reasons.

It is therefore an object of the present invention to remedy this and to improve an observation instrument of the type mentioned in the introduction having a viewing direction which deviates from the rectilinear viewing direction, to the effect that so much image information can be introduced that the capabilities even of high-resolution image sensors can be utilized, in particular image sensors having pixel sizes of less than 3 µm.

SUMMARY OF THE INVENTION

The object is achieved according to the invention by virtue of the fact that the distal deflection prism has a section extending laterally beyond the external diameter of the cylindrical section of the lens system, and that the image entrance plane of the image sensor runs approximately parallel to the optical axis.

These measures have various advantages. The cylindrical section of the optical lens system can have or include such a size which suffices for still maintaining a sufficient interspace, be it a ring-shaped or a crescent-shaped interspace, in the hollow body.

By virtue of the fact that the distal deflection prism disposed upstream of said optical lens system on the image entrance side extends laterally beyond the external diameter of the cylindrical section, it is possible to couple more image information into the optical lens system via the deflection prism than by means of a distal deflection prism which extends only within the diameter of the optical system, since the imaging-generating beam path in the prism runs partly outside the cylindrical section of the optical lens system. As a result, more image information can be conducted to the high-resolution image sensor by means of the optical lens system. In this case, neither the diameter of the hollow body need be increased, nor is the interspace alongside the optoelectronic image recording system significantly impaired, except at the distal end, at which the deflection prism extends laterally beyond the outer contour of the cylindrical section.

However, this extending laterally beyond does not occupy the entire interspace since it takes place only in a lateral direction. As a result, a sufficient interspace still remains available for example for leading optical waveguides or the like from a proximal to a distal end in the interspace in the hollow body. The optical waveguides can be led past the image recording system for example at the radially opposite side relative to the place of extending laterally beyond. It has been established that a corresponding longer embodiment of the distal deflection prism in the sense of laterally extending beyond the cross-sectional area of the optical system makes it possible to feed to the optical lens system so much image information that even high-resolution image sensors can be optimally utilized.

The result is that with the shank diameter remaining the same and with an ultimately unchanged diameter of the cylindrical section of an optical lens system by means of this configuration of the distal deflection prism, significantly sharper or higher-resolution images are possible. By utilizing that section of the distal deflection prism which extends laterally beyond the external diameter of the lens system for the beam path, a large viewing angle with a high numerical aperture is possible in the case of an oblique-viewing optical unit. The observation result can thereby be significantly improved. That is of great importance in the case of observation instruments having a viewing direction that deviates from the 0° viewing direction because with such instruments it is possible to obtain an all-round view in a hollow organ, for example a bladder, which can now be achieved with a high-resolution image quality.

The image entrance plane of the image sensor runs parallel to the optical axis. A proximal or second deflection prism is interposed in order that the image information on the image exit side from the optical lens system is correspondingly deflected onto the image entrance plane of the image sensor.

In one configuration of the invention, the image entrance plane of the image sensor is offset radially outwards relative to the cylindrical section of the lens system.

Since, according to the invention, the distal deflection prism extends laterally into a region and this region is then no longer suitable for rectilinearly leading through an instrument channel, the lateral region lying proximally behind the optical lens system can be used for accommodating the image sensor. Depending on how much space is available, its image entrance plane can then lie offset more or less laterally or radially outwards with respect to the cylindrical section of the lens system. In this case, the image sensor can also be inclined slightly relative to the optical axis. Advantageously, therefore, the distal deflection prism extends radially outwards in the same direction in which the image sensor is offset radially outwards.

It is also advantageous that a proximal deflection prism is arranged between optical lens system and image sensor, the image exit plane of said proximal deflection prism lying on the image entrance plane of the image sensor.

In a further configuration of the invention, the distal deflection prism has an aperture angle of greater than/equal to 50°.

Such a large aperture angle allows a large region to be examined.

In a further configuration of the invention, the distal deflection prism is constructed in such a way that beam expansion of less than/equal to 30% is effected within the deflection prism.

This measure has the advantage that an overdimensioned distal deflection prism is not required, that is to say that the latter has a relatively short construction as seen in the axial direction.

In a further configuration of the invention, a lens with negative refractive power is arranged upstream of the distal deflection prism and imparts a more parallel course to the entering.

This measure has the advantage that as a result of the parallelism the rays pass through the optical lens system in such a way that little shading or light reflected at the side surfaces is generated in the system, which light could impinge on the sensor as extraneous light and thereby impair the image resolution. This measure also allows a relatively compact design of the distal deflection prism.

In a further configuration of the invention, the interior of the hollow body, at least in the end region of the hollow body in which the optoelectronic image recording system is arranged, is divided by at least one separating web in such a way that the optoelectronic image recording system can be accommodated fittingly in a space arising as a result.

This measure has the advantage that now the possibility is afforded of providing a separate space in the hollow body as a result of the provision of the separating web, into which space the optoelectronic image recording system can be accommodated.

The separating wall can thus provide a hermetic separation relative to the interspace, into which the further components can be led through the hollow body or incorporated (e.g. optical waveguides).

The term "fittingly" means that the separating web separates the interior of the hollow body such that the entire optoelectronic image recording system, that is to say also with the laterally projecting distal deflection prism, can be fittingly accommodated in one space that arises as a result. On the other side of the separating web, the interspace is then present, through which the further components can be led through the hollow body or further components, such as optical waveguides, for example, can be accommodated. In the simplest case, only one separating web is present, which extends in the direction of the longitudinal extent of the hollow body, such that said separating web can be concomitantly produced, for example directly during the original production of the hollow body and is formed integrally with the hollow body. It is also possible for a plurality of separating webs to be provided; a space must at all events be designed such that the optoelectronic image recording system can be accommodated fittingly therein.

In a further configuration of the invention, the separating web is adapted to the outer contour of the laterally projecting section of the distal deflection prism.

As already mentioned, this laterally projecting section of the distal deflection prism projects laterally from the cylindrical section of the optical system, but only indeed on one side. If, as seen in cross section, the width of said section corresponds to the diameter of the cylindrical section of the optical system, then spaces are still available on the left and right of this radially laterally projecting section. If the separating web, as seen in cross section, is then adapted to this outer contour of the projecting section of the distal deflection prism, these spaces are available for other components over large length sections, if appropriate over the entire length section.

In a further configuration of the invention, the at least one separating web is embodied in such a way that the optoelectronic image recording system can be introduced for the purpose of mounting from distal to proximal into a space arising as a result of said separating web.

This measure has the advantage that the entire optoelectronic system can be prefabricated as a compact unit and can then be inserted from distal into the open shank or into the open space formed by the separating web.

In a further configuration of the invention, the radially laterally projecting section of the distal deflection prism extends right up to the separating web.

This measure has the advantage that depending on the viewing direction taken as a basis, it is possible to obtain an optimum coordination between the lateral extent of the section of the distal deflection prism and the geometry and position of the separating web. In this case, an air gap is left free having a size at least such that, as mentioned above, during mounting, by way of example, this structural unit can be inserted from distal into this space.

In a further configuration of the invention, the radially laterally projecting section of the distal deflection prism extends at least as far as a plane which is spanned by the image entrance plane of the image sensor. To put it the other way round, said image entrance plane of the image sensor lies at the level of the outer end of the laterally projecting section.

This geometry allows an advantageous arrangement of the image sensor and an optimum utilization of the resolution thereof.

In a further configuration of the invention, the radially laterally projecting section of the distal deflection prism extends beyond a plane spanned by the rear side of the image sensor.

The image sensor is usually a plate-shaped chip which can be arranged horizontally in a hollow body parallel to the longitudinal axis of the hollow body on account of its surface geometry. The lateral region, which cannot be utilized very much anyway as a result of the laterally projecting section of the distal deflection prism, can be occupied by the image sensor in a further proximal section.

It goes without saying that the features mentioned above and those yet to be explained below can be used not only in the combinations indicated, but also in other combinations or by themselves, without departing from the scope of the present invention.

BRIEF DESCRIPTION OF THE DRAWINGS

The invention is described and explained in greater detail below on the basis of some selected exemplary embodiments in association with the accompanying drawings, in which.

DESCRIPTION OF PREFERRED EMBODIMENT

Figure 1:
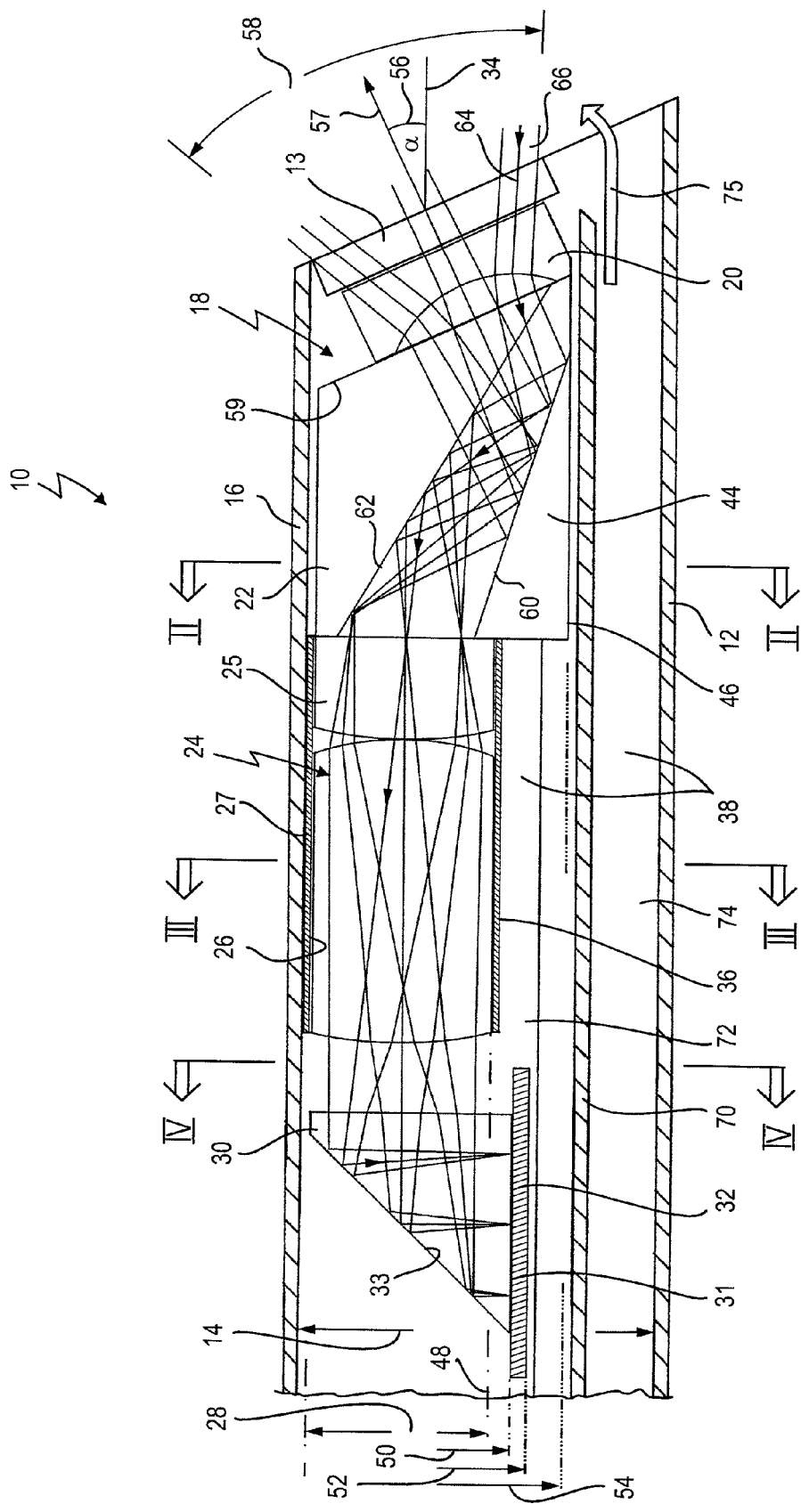
FIG. 1 shows a longitudinal section of a distal end region of an observation instrument according to the invention along a line I-I as illustrated in FIG. 3.

An exemplary embodiment of an observation instrument as illustrated in FIGS. 1 to 5 is designated in its entirety by the reference numeral 10.

The observation instrument 10 has a rectilinearly running stiff hollow body in the form of a hollow shank 12 having a specific internal diameter 14. The hollow body can be just a short stub or an elongated shank. The shank can be rigid or flexible. An optoelectronic image recording system 18 is accommodated in a distal end region 16 of the hollow shank 12. The hollow shank is closed off distally by means of a cover glass 13, which forms a sealing termination of the distal end of the hollow shank 12 by means of cement materials (not illustrated here). The cover glass 13 is transparent and thus allows entry of an observation light, that is an image which is to be acquired by the observation instrument 10.

The optoelectronic image recording system 18 has a negative lens 20, which on one side adjoins the inner side of the cover glass 13. On the other side, the negative lens 20 rests on a distal first deflection prism 22.

Proximally, the deflection prism 22 is continued by a customary optical lens system 24 composed of a multiplicity of lenses 25.

Said optical lens system 24 constitutes a cylindrical section 26 accommodated in a sleeve 27 surrounding the latter.

The external diameter 28 of the cylindrical section 26 is significantly smaller, approximately half, than the internal diameter 14 of the hollow shank 12.

Figure 3:
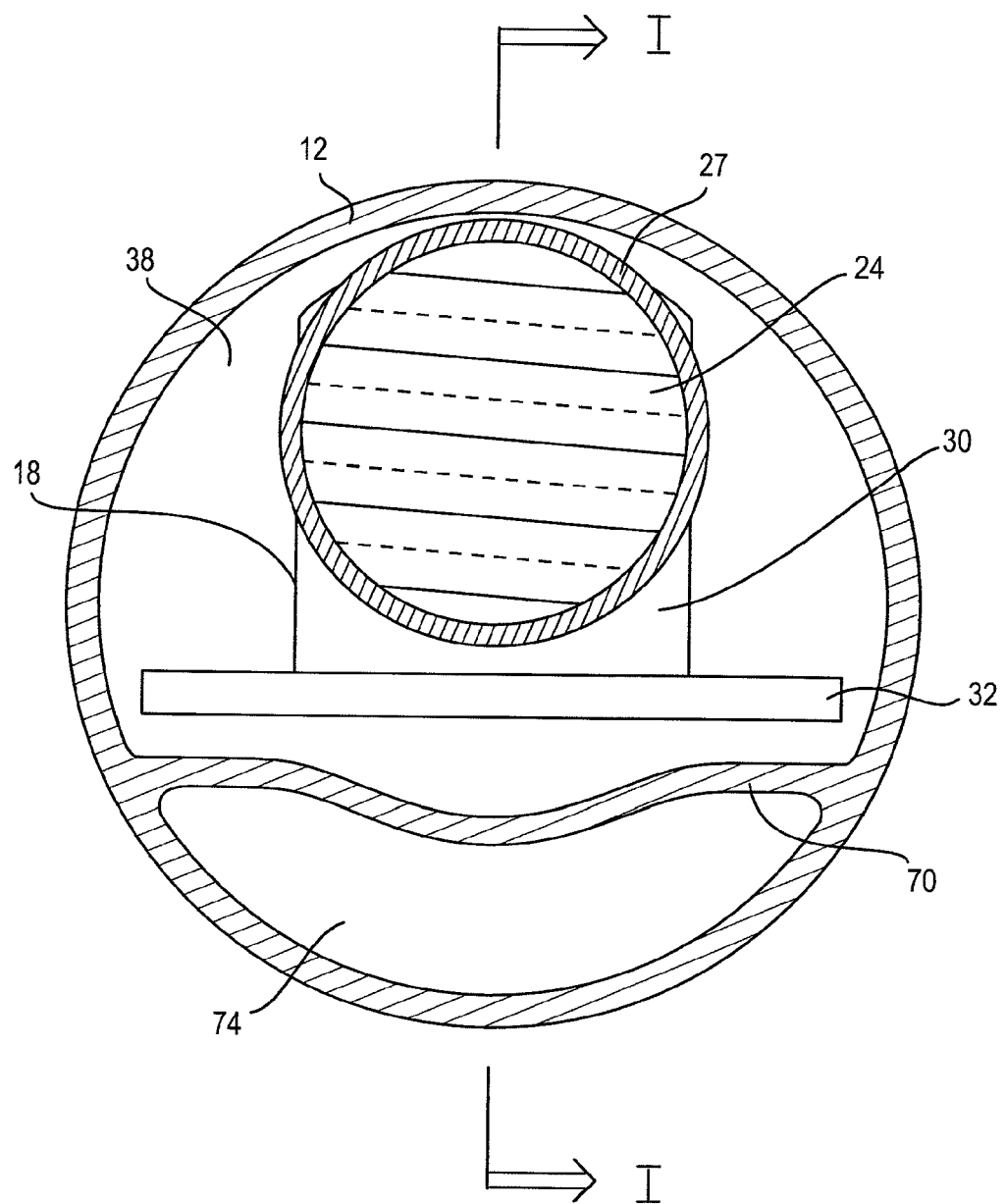
FIG. 3 shows a cross section along the line III-Ill in FIG. 1.

The optical lens system 24 or the sleeve 27 surrounding its cylindrical section 26 is arranged in the hollow shank 12 in such a way that, as can be seen in particular from the cross section in FIG. 3, an outer surface line of the sleeve 27 becomes located on an inner surface line of the inner side of the hollow shank 12.

This gives rise to an approximately crescent-shaped interspace 38 around said cylindrical section 26 of the optical lens system 24.

The optical axis 34, as can be seen in particular from FIG. 1, extends in the direction of the longitudinal axis of the hollow shank 12, but in a manner correspondingly laterally offset with respect thereto.

Proximally, the optical lens system 24 is followed by a proximal second deflection prism 30, which is provided for deflecting the image coming from the optical lens system 24 by 90° onto an image sensor 32. In this case, the image exit surface 31 of the proximal deflection prism 30 lies directly on the image entrance plane 50 of the image sensor. The proximal deflection prism 30 has a deflection surface 33 situated at an angle of 45° with respect to the optical axis 34, in order thus to bring about a 90° deflection of light rays which leave the optical lens system 24 proximally.

The distal end of the observation instrument 10 is designed such that it allows an oblique-viewing angle 56 of 25° relative to the optical axis 34. The cover glass 13 and the negative lens 20 are likewise situated at this oblique-viewing angle α, such that light or image information from this viewing angle can enter into the image recording system 18 or be picked up by the latter.

The aperture angle 58 of the image recording system is 50° or more.

Figure 2:
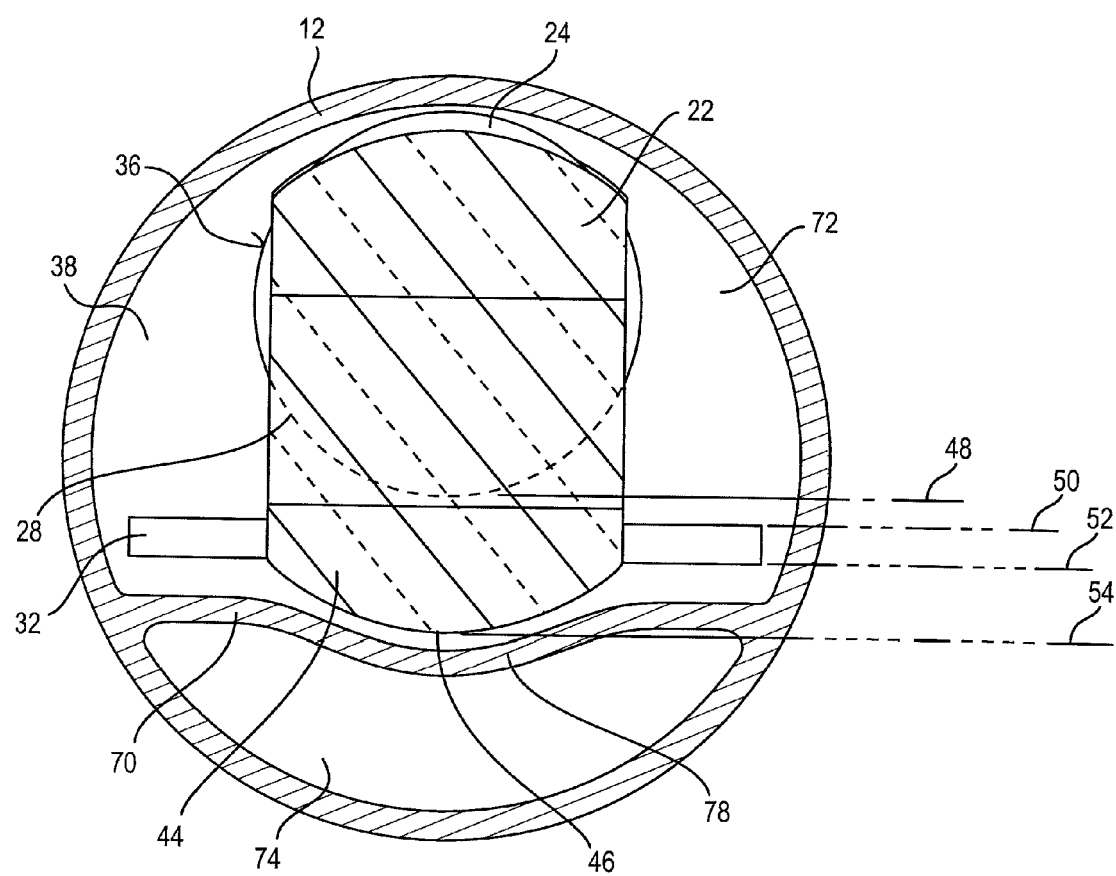
FIG. 2 shows a cross section along the line II-II in FIG. 1.

It can be discerned in particular from the sectional illustrations in FIGS. 1 and 2 that the distal deflection prism 22 has a section 44 which extends radially beyond the outer contour of the cylindrical section 26 of the optical lens system 24.

Furthermore, it can be discerned from FIG. 1 that said section 44 also extends beyond the image entrance plane 50 of the image sensor 32. Furthermore, it can be discerned that said section 44 also extends beyond the rear side 42 of the image sensor 32, that is to say also beyond the plane 52 spanned by said rear side.

Furthermore, FIG. 2 reveals that said section 44 extends very near to a separating web 70, which divides the interior of the hollow shank 12 into a first space 72, which accommodates the optoelectronic image recording system 18, and a second space 74. It is now possible to additionally utilize the projecting section 44 for the beam path. This opens up a large viewing angle with a high numerical aperture in the case of such oblique-viewing optical units.

It can be discerned in particular from the section illustration in FIG. 2 that the laterally projecting section 44 of the distal deflection prism 22 is rounded at its outer end.

Therefore, in this region, too, the separating web 70 is provided with a corresponding curvature 78.

In this case, the curvature 78 is adapted to this contour of the outer edge 46 of the laterally projecting section 44 of the distal deflection prism 22.

As can be gathered from FIGS. 1 and 2, this edge 46 thus extends right up to a plane 54 spanned by the maximum lateral extent of the section 44.

In FIG. 1, an arrow 75 indicates that in the space 74 created by the separating wall 70, further components, for example optical waveguides, can be arranged in order to feed illumination light to the distal end of the observation instrument 10. It can also be discerned from FIG. 1 that the separating wall 70 ends somewhat before the chamfered end of the hollow shank 12, such that said optical waveguides, as can be gathered from the curvature of the arrow 75, can be guided here in a correspondingly curved manner, that is parallel to the viewing direction 57. The distal ends of the optical waveguides (not illustrated here) are then embedded into corresponding cements as usual and form together with the cover glass 13 a sealed termination of at least the space 72. LEDs which generate and emit the illumination light can also be arranged at the distal end region. Their supply lines are guided to proximal in the space 74. The cover glass 13 together with the separating web 70 forms a distal termination of the space for the optoelectronic image recording system 18.

Figure 4:
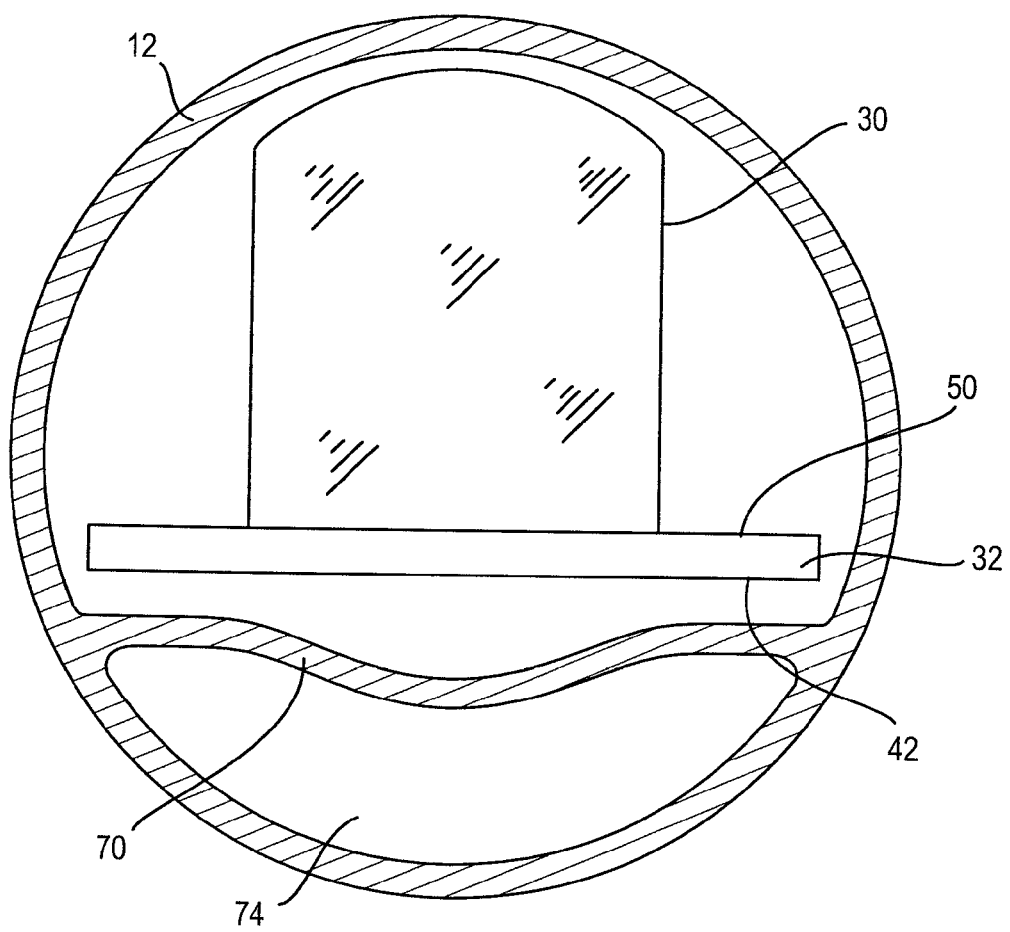
FIG. 4 shows a cross section along the line IV-IV in FIG. 1.

It can be seen in particular from the sectional illustrations in FIGS. 2, 3 and 4 that "alongside" the image recording system at least in the region of the optical lens system 24 and the deflection prisms 22 and 30 there is still enough space available, for example the interspace 38, for accommodating for example further components there, for example optical waveguides.

The functioning of the observation instrument is now as follows.

FIG. 1 illustrates three beams representing two laterally outer beams and one middle central beam. The centre ray 64 of the lower beam 66 illustrated in FIG. 1 is provided with an arrow, such that the beam path can be traced with the aid of said centre ray 64.

The incident light and the image information enter into the negative lens 20 through the cover glass 13. This front lens is a negative lens on account of the large aperture angle. Although the negative lens extends the individual beams somewhat, it parallelises the beams considerably with respect to one another. The more parallel the beams run within the distal deflection prism 22, the more compactly the latter can be constructed. As a result, a higher numerical aperture can be guided through the deflection prism 22. A higher numerical aperture, as required for image sensors having a small pixel frequency, leads in turn to a larger beam diameter. A larger beam diameter causes a relatively large ellipse in the case of reflections at inclined surfaces. The flatter the reflection surface is situated, the larger the reflection region.

The distal deflection prism 22 is constructed from three sections 22a, 22b and 22c.

The incident rays 64 impinge on the first reflection surface 60 and are reflected from the latter in the direction of the second reflection surface 62, where the rays impinge at an angle greater than the critical angle of total internal reflection. The second reflection surface 62 totally reflects the chief ray 64 of the centre beam, such that said chief ray runs collinearly with the optical axis 34 of the downstream optical lens system.

The entrance surface 59 is always oriented perpendicularly to the viewing direction 57. The inclination of the first reflection surface 60 is determined by way of the angle of the impinging rays after reflection at the second reflection surface 62 and the respective viewing direction. The inclination of the second reflection surface 62 is determined from the refractive index ratios of the three prism sections 22a, 22b and 22c and the beam diameter.

Figure 5:
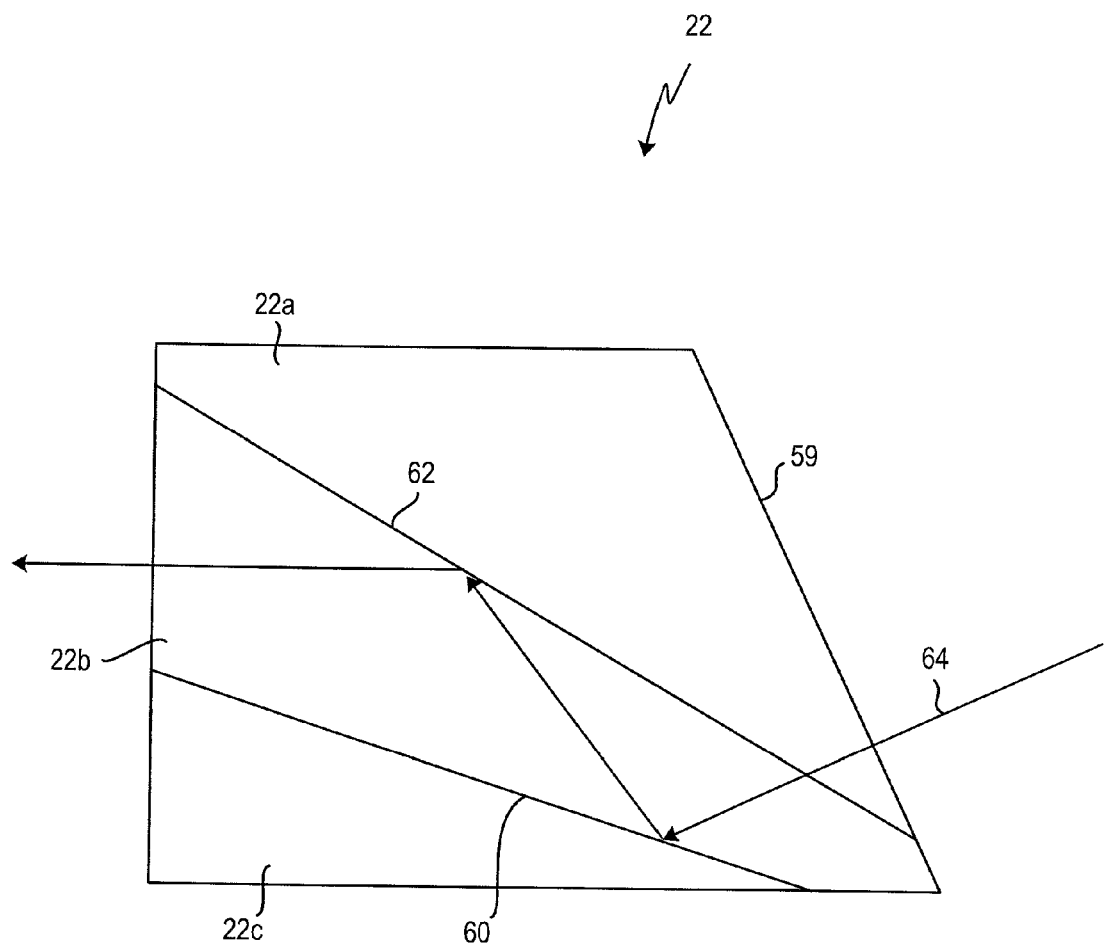
FIG. 5 shows the distal deflection prism and the beam path therein.

It can be seen from the illustration in FIG. 5 that only the sections 22a and 22b are optically active. The section 22c is merely accorded a mechanical significance. That is to say that the entire arrangement would function even without the section 22c, but the latter is advantageous for the overall stability of the prism. In addition, the section 22c affords protection for the rear surface and the edges of the partial section 22b.

In the distal deflection prism 22 care is taken to ensure that an expansion of the beams takes place, but said expansion should be a maximum of 30%.

In the optical lens system 24, the beam guiding is such that as far as possible no reflections take place at the circumferential edge, and so as a result no extraneous light arises which could lead to unsharpness on the image sensor 32. The beams emerging from the optical lens system 24 are deflected by 90° at a reflection surface 33 of the proximal second deflection prism 30, said reflection surface being situated at 45° with respect to the optical axis 34, and are directed onto the image entrance plane 50 of the image sensor 32.

The arrangement of the distal first deflection prism 22 with its radially laterally projecting section 44 and the subsequent lens system 24 allows a high-resolution image to be generated. In other words, the aperture angle, that is to say the numerical aperture of the beams 66, etc., has a magnitude such that a highly sharp image, in particular having a pixel size of less than 3 µm, can be generated on the image sensor 32.

The invention claimed is:

1. An observation instrument, comprising:
a hollow body having a longitudinal axis and an internal diameter, and further having an end region,
an optoelectronic image recording system arranged in said end region of said hollow body and having an image entrance side,
said optoelectronic image recording system comprising at said image entrance side
an optical lens system having a cylindrical section and having subsequently an image sensor converting an image coming from said optical lens system into electrical signals,
said optical lens system having an optical axis extending along a direction of said longitudinal axis of said hollow body,
said cylindrical section of said optical lens system having an external diameter being less than said internal diameter of said hollow body, thereby an interspace remains between an inner side of said hollow body and an outer side of said optical lens system, said interspace configured to lead further components in said hollow body,
an image system of said optoelectronic image recording system having a forward-oblique viewing direction deviating between 0° and 90° from said optical axis, said image system comprising at least one optical element, and
a distal deflection prism arranged both downstream of said at least one optical element and on an image entrance side of said optical lens system,
wherein said distal deflection prism has a section extending laterally beyond said external diameter of said cylindrical section of said optical lens system,
wherein an image entrance plane of said image sensor runs approximately parallel to said optical axis of said optical lens system, and
wherein said cylindrical section, said distal deflection prism, and said optical element are aligned such that an axis parallel to said longitudinal axis intersects with said cylindrical section, said distal deflection prism, and said optical element.

2. The observation instrument of claim 1, wherein an image entrance plane of said image sensor is offset radially outwards beyond said cylindrical section of said optical lens system.

3. The observation instrument of claim 2, wherein said distal deflection prism extends radially outwards laterally in a same direction in which said image sensor is offset outwards.

4. The observation instrument of claim 1, wherein a proximal deflection prism is arranged between said optical lens system and said image sensor, an image exit surface of said proximal deflection prism lying on an image entrance plane of said image sensor.

5. The observation instrument of claim 1, wherein said distal deflection prism has an aperture angle of greater than/equal to 50°.

6. The observation instrument of claim 1, wherein said distal deflection prism is constructed in such a way that a beam expansion of less than/equal to 30% is effected within said deflection prism.

7. The observation instrument of claim 1, wherein the at least one optical element comprises a lens with negative refractive power that is arranged upstream of said distal deflection prism and that imparts a more parallel course to entering rays.

8. The observation instrument of claim 1, wherein an interior of said hollow body, at least in said end region of said hollow body in which said optoelectronic image recording system is arranged, is divided by at least one separating web in such a way that said optoelectronic image recording system can be accommodated fittingly in a space arising as a result.

9. The observation instrument of claim 8, wherein said at least one separating web is adapted to an outer contour of a radially laterally projecting section of said distal deflection prism.

10. The observation instrument of claim 9, wherein said at least one separating web is embodied in such a way that said optoelectronic image recording system can be introduced for a purpose of mounting from distal to proximal in a space arising as a result of said at least one separating web.

11. The observation instrument of claim 10, wherein said radially laterally projecting section of said distal deflection prism extends right up to said at least one separating web.

12. The observation instrument of claim 1, wherein said radially laterally projecting section of said distal deflection prism extends at least as far as a plane which is spanned by an image entrance plane of said image sensor.

13. The observation instrument of claim 12, wherein said radially laterally projecting section of said distal deflection prism extends beyond a plane spanning by a rear side of said image sensor opposite to said image entrance plane.

14. The observation instrument of claim 1, wherein said interspace is configured to at least partially surround said cylindrical section of said optical lens system.

15. An observation instrument, comprising:
a hollow body having a longitudinal axis and an internal diameter, and further having an end region,
an optoelectronic image recording system arranged in said end region of said hollow body and having an image entrance side,
said optoelectronic image recording system comprising at said image entrance side
an optical lens system having a cylindrical section and having subsequently an image sensor converting an image coming from said optical lens system into electrical signals,
said optical lens system having an optical axis extending along a direction of said longitudinal axis of said hollow body,
said cylindrical section of said optical lens system having an external diameter being less than said internal diameter of said hollow body, thereby an interspace remains between an inner side of said hollow body and an outer side of said optical lens system, said interspace configured to lead further components in said hollow body,
an image system of said optoelectronic image recording system having a direction of view, said image system comprising at least one optical element, and
a distal deflection prism arranged both downstream of said at least one optical element and on an image entrance side of said optical lens system, wherein
said distal deflection prism has a section extending laterally beyond said external diameter of said cylindrical section of said optical lens system,
an image entrance plane of said image sensor runs approximately parallel to said optical axis of said optical lens system, and
said cylindrical section, said distal deflection prism, and said optical element are aligned such that an axis parallel to the longitudinal axis intersects with said cylindrical section, said distal deflection prism, and said optical element.

16. The observation instrument of claim 15, wherein an interior of said hollow body, at least in said end region of said hollow body in which said optoelectronic image recording system is arranged, is divided by at least one separating web in such a way that said optoelectronic image recording system can be accommodated in a space defined by said hollow body and said at least one separating web.

17. The observation instrument of claim 16, wherein said at least one separating web is adapted to an outer contour of a radially laterally projecting section of said distal deflection prism.

18. The observation instrument of claim 17, wherein the at least one optical element comprises:
a transparent cover defining at least an edge portion of said end region of the hollow body; and
a lens with negative refractive power arranged upstream of said distal deflection prism and downstream of said transparent cover.

19. The observation instrument of claim 18, wherein an aperture angle of said distal deflection prism is at least 50° and said distal deflection prism is configured such that a beam expansion of no more than 30% is effected within said deflection prism.

20. The observation instrument of claim 19, wherein said image system is configured with a forward-oblique direction of view between 0° and 90° and said observation instrument is at least one of an endoscope and an exoscope.

* * * * *